US011701387B2

(12) United States Patent
Bari et al.

(10) Patent No.: US 11,701,387 B2
(45) Date of Patent: Jul. 18, 2023

(54) CHIMERIC ANTIGEN RECEPTOR SPECIFIC FOR BDCA2 ANTIGEN

(71) Applicant: Miltenyi Biotec B.V. & Co. KG, Bergisch Gladbach (DE)

(72) Inventors: Rafijul Bari, Gaithersburg, MD (US); Markus Granzin, Germering (DE); Wing Leung, Boston, MA (US); Andrzej Dzionek, Overath (DE); Martin Meyer, Kürten (DE)

(73) Assignee: Miltenyi Biotec B.V. & Co. KG

( * ) Notice: Subject to any disclaimer, the term of this patent is extended or adjusted under 35 U.S.C. 154(b) by 269 days.

(21) Appl. No.: 16/959,330

(22) PCT Filed: Jan. 4, 2019

(86) PCT No.: PCT/EP2019/050123
§ 371 (c)(1),
(2) Date: Jun. 30, 2020

(87) PCT Pub. No.: WO2019/134950
PCT Pub. Date: Jul. 11, 2019

(65) Prior Publication Data
US 2020/0353003 A1    Nov. 12, 2020

Related U.S. Application Data

(60) Provisional application No. 62/613,632, filed on Jan. 4, 2018.

(51) Int. Cl.
*C07K 16/46*    (2006.01)
*A61K 35/17*    (2015.01)
(Continued)

(52) U.S. Cl.
CPC .......... *A61K 35/17* (2013.01); *A61K 39/3955* (2013.01); *A61P 35/00* (2018.01); *C07K 16/2851* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 9,815,901 B2 * | 11/2017 | Brogdon | C07K 16/28 |
| 10,611,843 B2 * | 4/2020 | Fournier | A61P 35/00 |
| 2020/0055941 A1 * | 2/2020 | Bürger | A61P 37/06 |

FOREIGN PATENT DOCUMENTS

| | | |
|---|---|---|
| WO | WO 2016/030414 | 3/2016 |
| WO | WO 2018/185284 | 10/2018 |

OTHER PUBLICATIONS

Abate-Daga et al., CAR models_ next-generation CAR modifications for enhanced T-cell function Oncolytics 3:16014, doi:10.1038/mto.2016.14, 2016.*

(Continued)

*Primary Examiner* — Claire Kaufman
(74) *Attorney, Agent, or Firm* — Fish & Richardson P.C.

(57) ABSTRACT

The present invention discloses a chimeric antigen receptor (CAR) comprising an antigen binding domain specific for BDCA2, a population of engineered cells expressing said CAR and a pharmaceutical composition thereof. Said engineered cells are for treatment of cancer in a subject, wherein the cancerous cells of said cancer express BDCA2 such as Blastic Plasmacytoid Dendritic Cell Neoplasm (BPDCN).

7 Claims, 6 Drawing Sheets

Specification includes a Sequence Listing.

A) Anti-BDCA-2 CAR cell construct diagram

B) NK cells     C) T cells

D) Reporter     E) RS4-11

(51) Int. Cl.
*A61P 35/00* (2006.01)
*A61K 39/395* (2006.01)
*C07K 16/28* (2006.01)

(56) References Cited

OTHER PUBLICATIONS

Riaz et al., Blastic plasmacytoid dendritic cell neoplasm: Update on molecular biology, diagnosis, and therapy, Canc. Control, 21(4): 279-, Oct. 2014.*

Pelllerin et al., Anti-BDCA2 monoclonal antibody inhibits plasmacytoid dendritic cell activation through Fc-dependent and Fc-independent mechanisms, EMBO Mol. Med. 7(4):464-476, 2015.*

Boiocchi et al., BDCA-2 (CD303): a highly specific marker for normal and neoplastic plasmacytoid dendritic cells, Blood, 122(2):296-297, Jul. 11, 2013.*

Glienke et al., Advantages and applications of CAR-expressing natural killer cells, Frontiers Pharmacol. 6(21):1-7, doi.org/10.3389/fphar.2015.00021, Feb. 12, 2015.*

Cellectis, Cellectis submits IND application for UCART123, an allogeneic gene edited CAR-t cell . . . , Retrieved from: <URL:https://cellectis.com/en/press/cellectis-submits-ind-application-for-ucart123-an-allogeneic-gene-edited-car-t-cell-product-candidate-in-aml-and-bpdcn>. Retrived on May 9, 2022, Jan. 3, 2017.*

Walchi et al., A universal killer T-cell for adoptive cell therapy of cancer, Annals Oncol. 26(Supplement 8):viii1-viii4, doi:10.1093/annonc/mdv513, 2015.*

ClincalTrials.gov Study NCT02159495 (v9), Retrieved from: <URL:https://clinicaltrials.gov/ct2/history/NCT02159495?V_9=View#StudyPageTop>. Retrieved on May 6, 2022. Jun. 24, 2016.*

Irving et al., Engineered chimeric antigen receptor T-cels from racing in solid tumors: Don't forget the fuel, Front. Immunol. 8:267, pp. 1-19, 2017.*

Bejestani et al., "Characterization of a switchable chimeric antigen receptor platform in a pre-clinical solid tumor model," Oncoimmunology, 2017, 6(10):e1342909.

Cai et al., "Pre-clinical studies of allogeneic anti-CD123 CAR T-cells for the therapy of blastic plasmacytoid dendritic cell neoplasm (BPDCN)," Blood, 2017, 130(Suppl 1):2625.

Cartellieri et al., "Switching CAR T cells on and off: a novel modular platform for retargeting of T cells to AML blasts," Blood Cancer Journal, 2016, 6(8):e458.

International Search Report and Written Opinion in PCT Application. No. PCT/EP2019/050123, dated May 16, 2019, 17 pages.

Laribi et al., "Blastic plasmacytoid dendritic cell neoplasm: from origin of the cell to targeted therapies," Biology of Blood and Marrow Transplantation, 2016, 22(8):1357-1367.

Lohmueller et al., "mSA2 affinity-enhanced biotin-binding CAR T cells for universal tumor targeting," Oncoimmunology, 2017, 7(1):e1368604.

Lonardi et al., "P2.213: A monoclonal antibody anti-BDCA2 (CD303) highly specific for plasmacytoid dendritic cell neoplasms on paraffin sections," Virchows Archiv, 2009, 455(Suppl 1):S254-S255.

Oberschmidt et al., "Redirected primary human chimeric antigen receptor natural killer cells as an 'off-the-shelf immunotherapy' for improvement in cancer treatment," Frontiers in Immunology, 2017, 8:654.

Tamada et al., "Redirecting gene-modified T cells toward various cancer types using tagged antibodies," Clin. Cancer Res., 2012, 18(23):6436-6445.

Granzin et al., "Fully automated expansion and activation of clinical-grade natural killer cells for adoptive immunotherapy," Cytotherapy, May 1, 2015, 17(5):621-32.

Kawalekar et al., "Distinct signaling of coreceptors regulates specific metabolism pathways and impacts memory development in CAR T cells," Immunity, Feb. 16, 2016, 44(2):380-90.

International Preliminary Report on Patentability in International Application No. PCT/EP2019/050123, dated Jul. 7, 2020, 11 pages.

Roos-Weil et al., "Stem cell transplantation can provide durable disease control in blastic plasmacytoid dendritic cell neoplasm: a retrospective study from the European Group for Blood and Marrow Transplantation," Blood, The Journal of the American Society of Hematology, Jan. 17, 2013, 121(3):440-6.

Sadelain et al., "Therapeutic T cell engineering," Nature, May 2017, 545(7655):423-31.

Taylor et al., "Loss-of-function mutations in the splicing factor ZRSR2 are common in blastic plasmacytoid dendritic cell neoplasm and have male predominance," Blood, Nov. 15, 2013, 122(21):741, 3 pages (abstract).

Vardiman et al., "The 2008 revision of the World Health Organization (WHO) classification of myeloid neoplasms and acute leukemia: rationale and important changes," Blood, The Journal of the American Society of Hematology, Jul. 30, 2009, 114(5):937-51.

* cited by examiner

CHIMERIC ANTIGEN RECEPTOR SPECIFIC FOR BDCA2 ANTIGEN

CROSS-REFERENCE TO RELATED APPLICATIONS

This application is a 371 U.S. National Stage entry of International Application No. PCT/EP2019/050123, filed on Jan. 4, 2019, which claims priority to U.S. Provisional Patent Application Serial No. 62/613,632, filed on Jan. 4, 2018, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Jun. 30, 2020, is named Sequence Listing.txt and is 4862 bytes in size.

FIELD OF INVENTION

The present invention relates to the field of treatment of cancer, in particular to the treatment of cancer by using the antigen BDCA2 as a target.

BACKGROUND OF THE INVENTION

Blastic Plasmacytoid Dendritic Cell Neoplasm (BPDCN) is a rare disease of the bone marrow and blood. The term BPDCN refers to a malignant neoplasm, or cancer, that affects blastic, or immature, plasmacytoid dendritic cells. The World Health Organization standardized the term blastic plasmacytoid dendritic cell neoplasm in 2008, listing it under "acute myeloid leukemia and related neoplasms." (Vardiman J W et al., Blood. 2009). BPDCN affects multiple organs that include the skin and the lymph nodes. Unlike most other leukemias, BPDCN has a pronounced male predominance; approximately 75% to 90% of cases occur in men (Taylor J et al., Blood. 2013). Most patients survive for only 10 to 14 months after diagnosis, despite receiving various chemotherapeutic regimens (Roos-Weil D et al., Blood. 2013).

At present, there is no uniform, consensus, worldwide standard of care treatment for BPDCN. Some physicians treat this disease using chemotherapy regimens that are designed for AML and ALL, others treat the disease like non-Hodgkin lymphoma. Using of multiple—agent, intensive chemotherapy initially produce remission, however relapse tends to occur quickly. Most patients survive only 10-14 months after diagnosis, despite receiving various chemotherapeutic regimens. However, the use of bone marrow transplant is reported to improve median survival to two to four years (Roos-Weil D et al., Blood. 2013).

Chimeric antigen receptor (CAR) T cells have proven that engineered immune cells can serve as a powerful new class of cancer therapeutics (Sadelain M et al., Nature. 2017). The technique has now been tested in multiple clinical trials, with spectacular results, often resulting in complete remission. CAR-engineered NK cells also showed promising results in pre-clinical investigation. Plasmacytoid dendritic cells specifically express anti-BDCA2. BDCA2 (CD303) is also proposed to be a marker for BPDCN (Boiocchi L et al., Blood 2013).

There is a need in the art for an improved or alternative treatment of cancer like malignant nesoplasm such as BPDCN.

SUMMARY OF THE INVENTION

The inventors have engineered NK and T cells expressing a chimeric antigen receptor that is specific for the antigen BDCA2 ("BDCA2-CAR") which is highly expressed in BPDCN cancerous cells. Surprisingly, the engineered CAR-NK and -T cells can specifically kill BDCA2 expressing cells, which are highly resistant to their natural killing, with high efficiency (see FIG. 2). Since BDCA-2 is known to be expressed only in plasmacytoid dendritic cells, the engineered immune cells (NK and T cells) expressing a BDCA2 CAR will specifically kill the BDCA2 expressing cancerous cells such as the BPDCN in recipients. The inventors also found that the BDCA2-CAR NK cells secrete less cytokines than CAR T cells (see FIG. 3) indicating less cytokine release syndrome (CRS) in a subject to be treated with such cells. This suggest that the BDCA2-CAR NK cells will be less toxic and safer than BDCA2-CAR T cells in patients. Moreover, NK cells are short lived, thus no CAR-NK cells are expected to persist in recipient body after two months of treatments and the short lifespan will additionally reduce the toxicity. Therefore, BDCA2-CAR NK cells may be even preferred compared to BDCA2-CAR T cells for the treatment of BPDCN although both kinds of engineered cell types efficiently kill BDCA2 target cells.

BRIEF DESCRIPTION OF THE DRAWINGS

(FIG. 1A) BDCA2 CAR construct comprised of a EF1a promoter, BDCA-2 binder with unique linkers, hinge and transmembrane region from the CD8 receptor, the 4-1BB transactivating domain, and the CD3 zeta signaling domain. Expression of a BDCA2 CAR in NK (FIG. 1B) and T (FIG. 1C) -cells were detected using specific idiotype raised against aBDCA-scFV. BDCA-2 expression in reporter (mouse A95-KK) and RS4-11 (FIG. 1D and FIG. 1E, respectively) cell lines were detected using mAB specific for BDCA2.

Flow cytometry based cytotoxicity assay was performed to assess the cytotoxicity of CAR-NK and CAR-T cells against target cells expressing BDCA2. Reporter (A95-KK) and RS4-11 cells without expressing BDCA2 are used as control target cells (reporter-control and RS4-11-control, respectively). Reporter and RS4-11 stably expressing BDCA2 are used as target cells (Reporter-BDCA2 and RS4-11-BDCA2). Engineered NK and T-cells expressing BDCA2 CAR were used to assess the specific killing whereas non-transduced NK and T-cells (untransduced) used as negative control.

Figure 3:
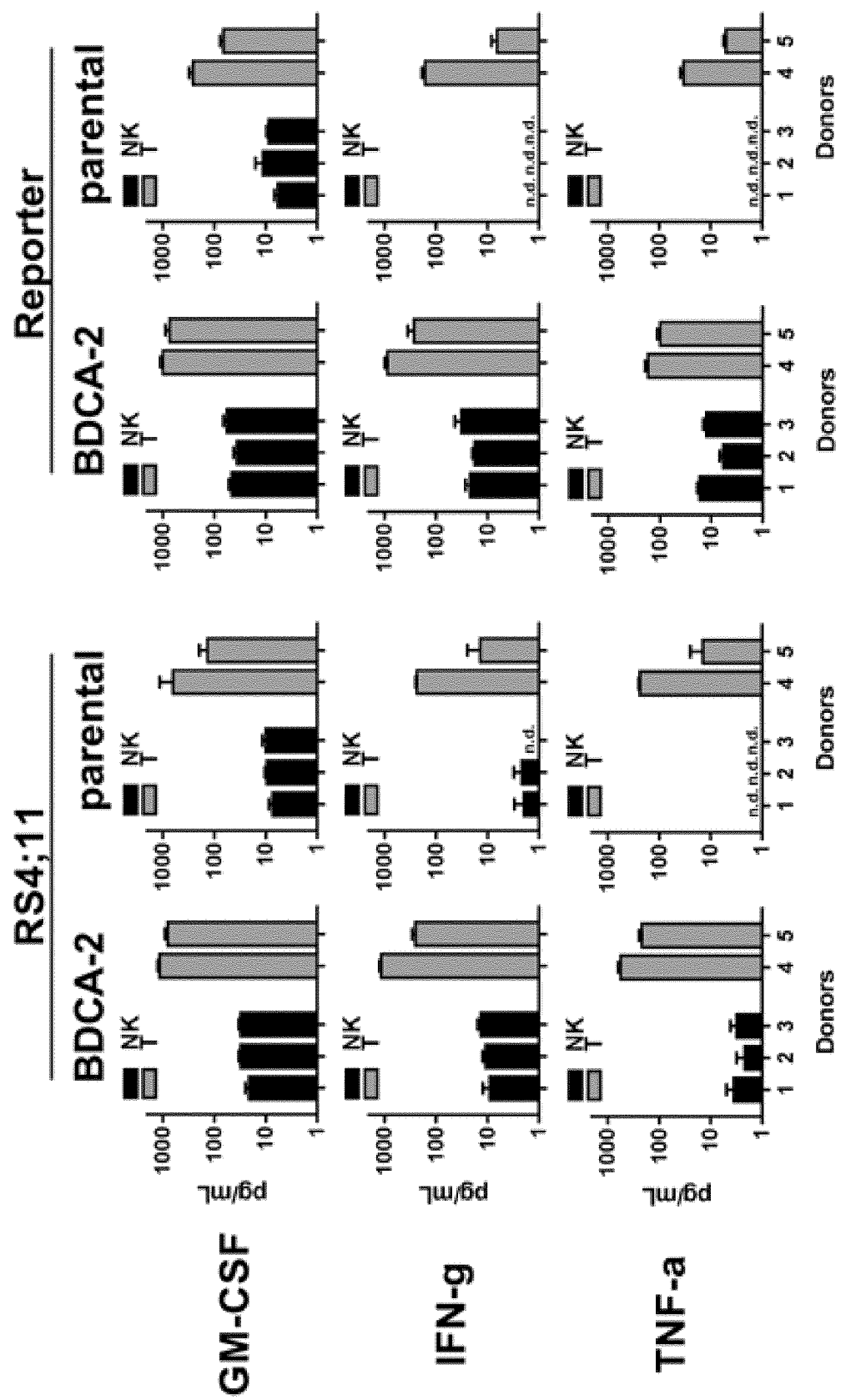

FIG. 3: CAR-T cells produce significantly higher amount of cytokines compared to CAR-NK cells when co-culturing with target cells expressing BDCA2.

Cytokine production of CAR-NK and CAR-T cells were assessed 24 hrs after co-culturing them with target cells using MACSPlex cytokine kits from Miltenyi Biotec. BDCA2 indicate target cells expressing BDCA2; Parental indicate target cells without BDCA2.

Figure 4:
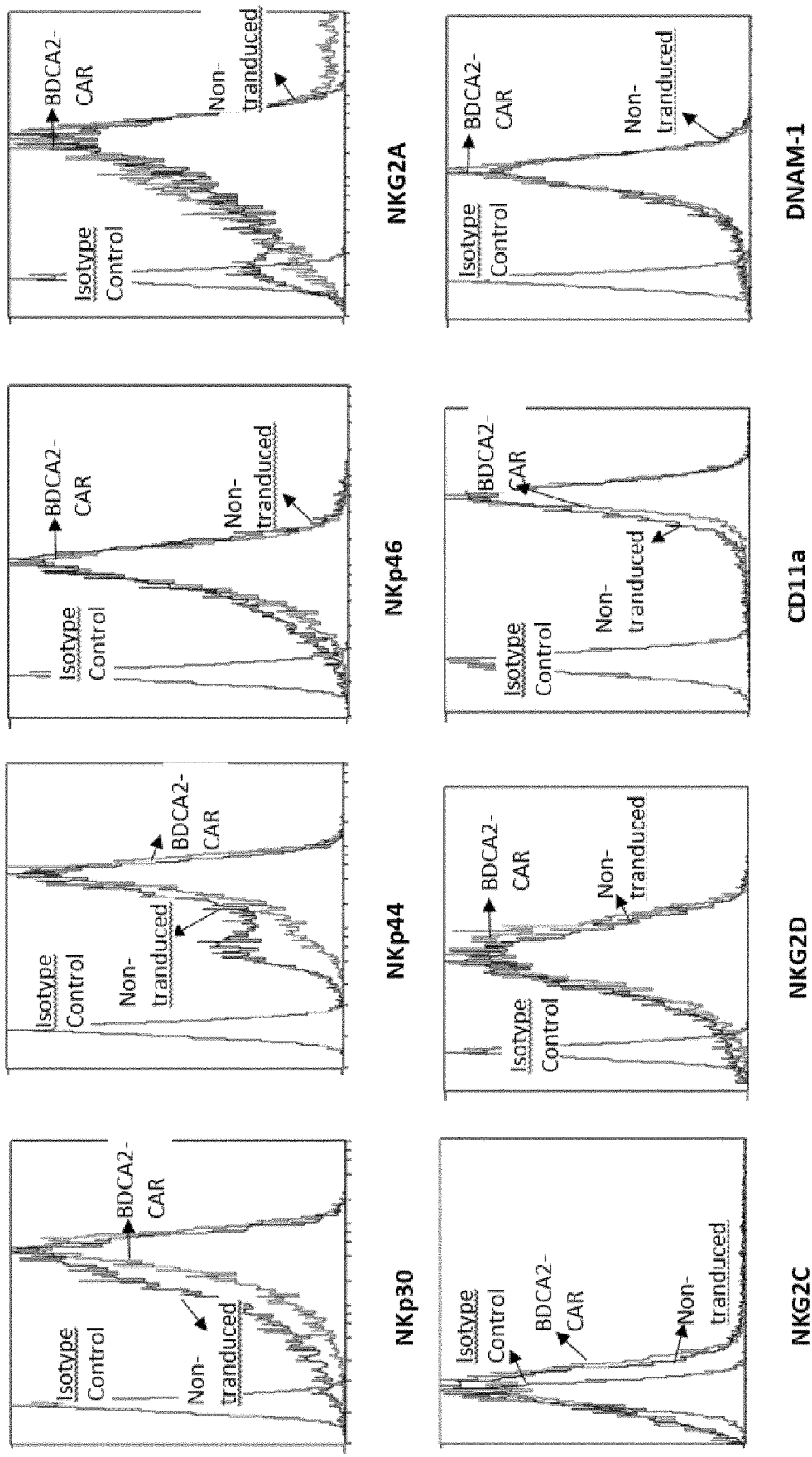

FIG. 4: Expression of common NK cell receptors in non-transduced and BDCA2-CAR transduced NK cells were determined by flow cytometry on day 8 after transduction. There is no significant alteration of NK cell phenotype upon BDCA2 transduction.

Figure 5:
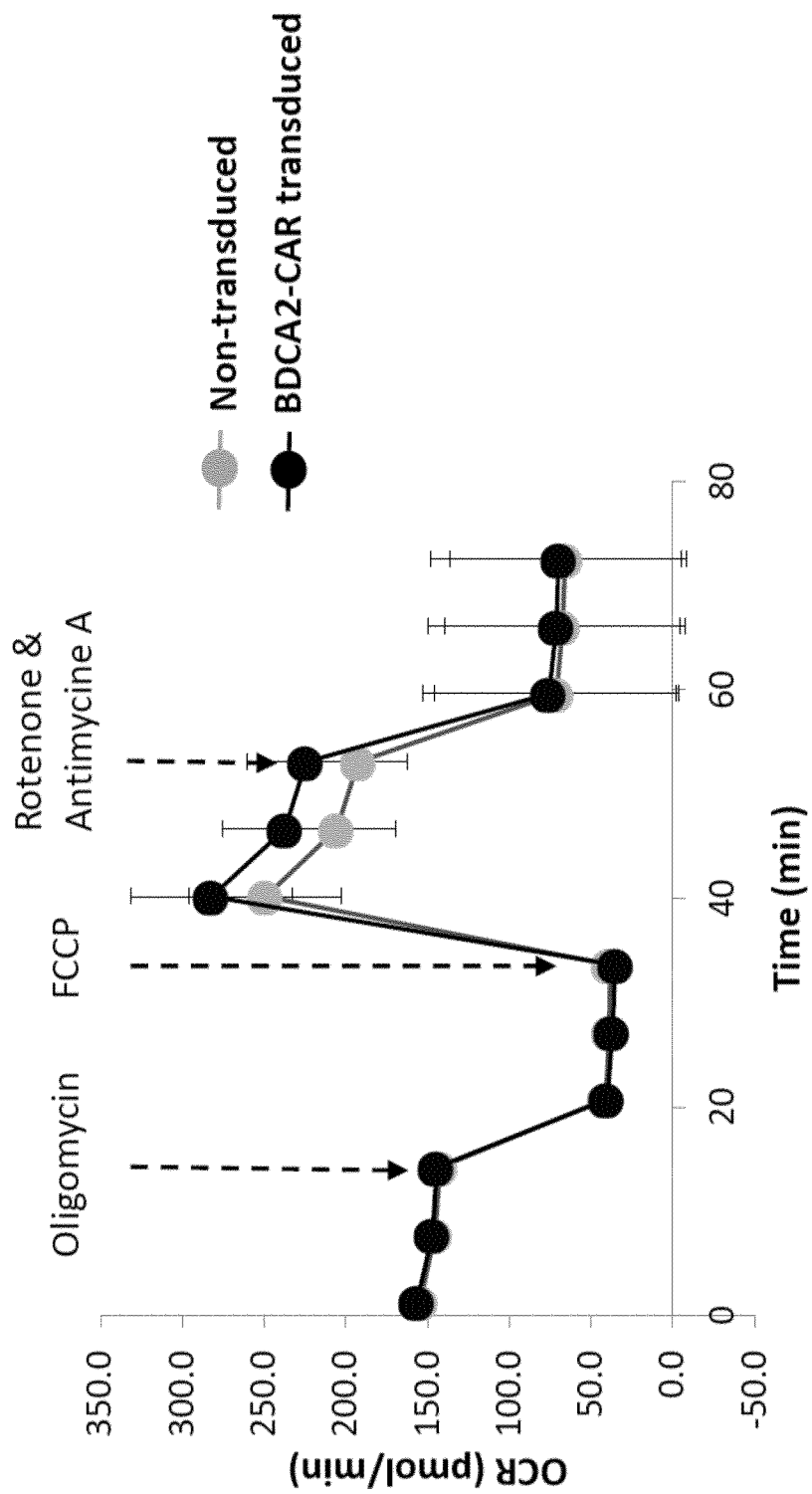

FIG. 5: The oxygen consumption rate (OCR) of non-transduced and BDCA2-CAR transduced NK cells on day 8 after transduction. Basal OCR was measured, followed by serial additions of oligomycin (an inhibitor of ATP synthesis), carbonyl cyanide-ptrifluoromethoxyphenylhydrazone (FCCP; an uncoupling ionophore), and rotenone with antimycin A (blocking agents for complexes I and III of the electron transport chain, respectively) to discern the relative contributions of mitochondrial and non-mitochondrial mechanism of oxygen consumption.

Figure 6:
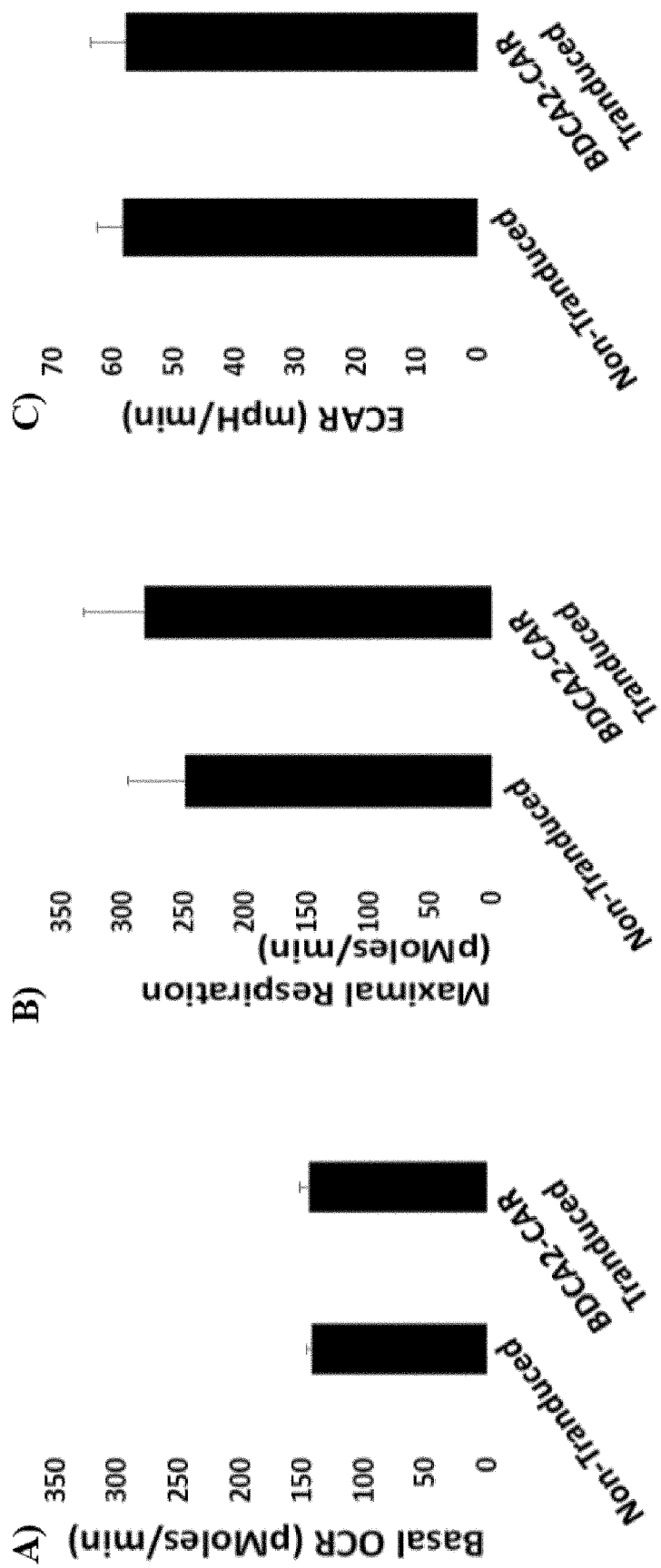

FIG. 6: There are no significant changes in cellular metabolism of NK cells upon transduction with BDCA2-CAR. The basal OCR levels (FIG. 6A) as well as the maximal respiratory levels (FIG. 6B) is similar between non-transduce and transduced cell on day 8 after transduction. There is no significant difference in extracellular acidification rate (ECAR) between non-transduced and transduced cells on day 8 after transduction (FIG. 6C).

DETAILED DESCRIPTION OF THE INVENTION

Surprisingly, we found that BDCA2 expressing cancerous cells which are directly targeted by an engineered immune cell expressing a CAR specific for the antigen BDCA2 are affected in a manner that these cells fail to grow and/or are prompted to die.

In a first aspect, the invention provides a chimeric antigen receptor (CAR) comprising an antigen binding domain specific for the antigen BDCA2 ("BDCA2-CAR").

The antigen binding domain of said BDCA2-CAR may comprise, for example, full length immunoglobulin heavy and/or light chain(s), Fab fragments, single chain Fv (scFv) fragments, divalent single chain antibodies or diabodies, each of which are specific for the target antigen BDCA2.

The antigen binding domain of said BDCA2-CAR may comprise the amino acid sequences of SEQ ID NO:1 and SEQ ID NO:2. The order (orientation) of these two sequences within the antigen binding domain of the BDCA2-CAR may be from the N-terminus to the C-terminus SEQ ID NO:1—SEQ ID NO:2 or SEQ ID NO:2—SEQ ID NO:1, preferentially the order within the antigen binding domain of the BDCA2-CAR may be from the N-terminus to the C-terminus SEQ ID NO:1—SEQ ID NO:2. It was surprising that the orientation from the N-terminus to the C-terminus SEQ ID NO:1—SEQ ID NO:2 works better than the order SEQ ID NO:2—SEQ ID NO:1. The antigen binding domain of said BDCA2-CAR may comprise a scFv comprising the amino acid sequence of SEQ ID NO:4.

Said CAR may comprise a transmembrane domain and an intracellular signaling domain. Said intracellular signaling domain may comprise at least an immunoreceptor tyrosine-based activation motif (ITAM). Said intracellular signaling domain may comprise at least a primary signaling domain such as CD28, CD137, OX40 or CD3zeta. Said transmembrane domain may comprise e.g. a sequence of the transmembrane domains derived from CD8alpha and/or CD28. Said intracellular signaling domain also may comprise a co-stimulatory signaling domain such as CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

Alternatively, the CAR may be composed of further parts such as a linker and/or hinge and/or may be composed as di- or multi-chain CAR as described below.

The CAR may be a CAR, wherein said CAR may comprise
  i) an antigen binding domain specific for the antigen BDCA2
  ii) a transmembrane domain
  ii) an intracellular signaling domain comprising at least a primary signaling domain and at least a co-stimulatory domain.

In one aspect of the invention the BDCA2-CAR of the invention is for the use in treatment of cancer in a subject suffering from cancer, and wherein the cancerous cells of said cancer expresses BDCA2. The antigen binding domain of said BDCA2-CAR may comprise the amino acid sequences of SEQ ID NO:1 and SEQ ID NO:2. The antigen binding domain of said BDCA2-CAR may comprise a scFv comprising the amino acid sequence of SEQ ID NO:4.

Said cancer may be a malignant neoplasm such as Blastic Plasmacytoid Dendritic Cell Neoplasm (BPDCN).

In a preferred embodiment of the invention, the BDCA2 expressing cancerous cell is targeted by an engineered cell, preferentially T cell or NK cell, more preferentially a human T cell or NK cell, expressing a chimeric antigen receptor specific for BDCA2 as disclosed herein. This engineered T cell or NK cell may be used in adoptive T cell or NK cell therapy.

In an aspect, the invention provides a population of cells comprising genetically modified cells expressing a chimeric antigen receptor specific for the antigen BDCA2 (BDCA2-CAR) as disclosed herein. The antigen binding domain of said BDCA2-CAR may comprise the amino acid sequences of SEQ ID NO:1 and SEQ ID NO:2. The antigen binding domain of said BDCA2-CAR may comprise a scFv comprising the amino acid sequence of SEQ ID NO:4. Preferentially said population of cells comprising genetically modified cells expressing a chimeric antigen receptor specific for the antigen BDCA2 (BDCA2-CAR) is an isolated population of cells. Said modified cells may be immune cells, preferentially T cells or NK cells.

In one aspect, the invention provides a population or an isolated population of engineered cells expressing a BDCA2-CAR as disclosed herein for use in immunotherapy. The immunotherapy may be for treatment of cancer in a subject suffering from cancer, wherein the cancerous cells of said cancer express BDCA2. The antigen binding domain of said BDCA2-CAR may comprise the amino acid sequences of SEQ ID NO:1 and SEQ ID NO:2. The antigen binding domain of said BDCA2-CAR may comprise a scFv comprising the amino acid sequence of SEQ ID NO:4.

Said cancer may be a malignant neoplasm such as Blastic Plasmacytoid Dendritic Cell Neoplasm (BPDCN).

In case of need, said population or isolated population of engineered cells are expanded to therapeutically effective number of cells before use in said immunotherapy. Said cells may be immune cells or immune cell subsets, preferentially T cells or T cell subsets or NK cells or NK cells subsets.

In one aspect, the invention provides a method of treating cancer comprising administering to a subject in need thereof an amount of enriched, engineered cells expressing BDCA2-CAR as disclosed herein effective to treat said cancer. The treatment of cancer may be in a subject suffering from cancer, wherein the cancerous cells of said cancer express BDCA2. Said cancer may be a malignant neoplasm such as Blastic Plasmacytoid Dendritic Cell Neoplasm (BPDCN).

Said cells may be immune cells or immune cell subsets, preferentially T cells or T cell subsets or NK cells or NK cells subsets.

In one aspect, the invention provides a pharmaceutical composition comprising genetically modified cells expressing a CAR specific for the antigen BDCA2 as disclosed herein and a pharmaceutical acceptable carrier.

Said pharmaceutical composition may be used in the treatment of cancer in a subject suffering from cancer. Said cancer may be a malignant neoplasm such as Blastic Plasmacytoid Dendritic Cell Neoplasm (BPDCN).

In an aspect, the invention provides nucleic acids molecules and nucleic acids constructs such as vectors which encode for the BDCA2-CAR of the present invention as disclosed herein.

In another aspect the present invention provides a composition comprising
 a) an immune cell expressing a CAR comprising
  i) an antigen binding domain specific for a tag of a tagged polypeptide
  ii) a transmembrane domain
  iii) an intracellular signaling domain
  wherein said antigen binding domain specifically binds a tag of a tagged polypeptide, wherein said polypeptide binds specifically to the antigen BDCA2 expressed on the surface of a target cell, wherein said target cell is a cancer cell expressing BDCA2, and
 b) said tagged polypeptide.

Said cancer cell may be a malignant neoplasm such as Blastic Plasmacytoid Dendritic Cell Neoplasm (BPDCN).

Said immune cell may be a T cell or a NK cell.

Said CAR, wherein said intracellular signaling domain comprises at least a primary signaling domain such as CD3zeta and at least a co-stimulatory signaling domain such as CD137 or CD28.

The tag may be a hapten such as biotin or FITC or a peptide chemically or recombinantly coupled to said polypeptide. Tags for "anti-tagCAR systems" are well known in the art and any tag suitable for such a system of anti-tagCAR and tagged polypeptide may be used herein. The tagged polypeptide that binds to an antigen expressed on the surface of a cell may be an antibody or antigen binding fragment thereof. The tagged polypeptide may comprise the amino acid sequences of SEQ ID NO:1 and SEQ ID NO:2, or the amino acid sequence of SEQ ID NO:4.

In another aspect the present invention provides a pharmaceutical composition comprising
 a) an immune cell expressing a CAR comprising
 i) an antigen binding domain specific for a tag of a tagged polypeptide
 ii) a transmembrane domain
 iii) an intracellular signaling domain
 wherein said antigen binding domain specifically binds a tag of a tagged polypeptide, wherein said polypeptide binds specifically to the antigen BDCA2 expressed on the surface of a target cell, wherein said target cell is a cancer cell, and
 b) said tagged polypeptide.

Said pharmaceutical composition optionally may comprise a pharmaceutical acceptable carrier together with said immune cells and/or together with said tagged polypeptide.

In another aspect the present invention provides a composition for the use in the treatment of a subject suffering from cancer, wherein the cancer cells express BDCA2, preferentially the cancer may be a malignant neoplasm such as Blastic Plasmacytoid Dendritic Cell Neoplasm (BPDCN), the composition comprising
 a) an immune cell expressing a CAR comprising
 i) an antigen binding domain specific for a tag of a tagged polypeptide
 ii) a transmembrane domain
 iii) an intracellular signaling domain
 wherein said antigen binding domain specifically binds a tag of a tagged polypeptide, wherein said polypeptide binds specifically to the antigen BDCA2 expressed on the surface of a target cell, wherein said target cell is a cancer cell, and
 b) said tagged polypeptide.

In another aspect the present invention provides a method for treatment of a subject suffering from cancer, wherein the cancer cells express BDCA2, preferentially the cancer may be a malignant neoplasm such as Blastic Plasmacytoid Dendritic Cell Neoplasm (BPDCN), the method comprising the step of applying a CAR as disclosed herein comprising at least one antigen binding domain specific for the antigen BDCA2 to said patient, or of applying a composition as disclosed herein comprising
 a) an immune cell expressing a CAR comprising
 i) an antigen binding domain specific for a tag of a tagged polypeptide
 ii) a transmembrane domain
 iii) an intracellular signaling domain
 wherein said antigen binding domain specifically binds a tag of a tagged polypeptide, wherein said polypeptide binds specifically to the antigen BDCA2 expressed on the surface of a target cell, wherein said target cell is a cancer cell, and
 b) said tagged polypeptide.

In one embodiment of the invention the immune cells expressing the CAR specific for BDCA2 (the BDCA2-CAR) of the invention is for use in treatment of cancer in a subject suffering from cancer, wherein the cancerous cells of said cancer expresses BDCA2, e.g. a malignant neoplasm such as Blastic Plasmacytoid Dendritic Cell Neoplasm (BPDCN). Immune cells, e.g. T cells or NK cells of a subject are isolated. The subject may suffer from said cancer or may be a healthy subject. These cells are genetically modified in vitro or in vivo to express BDCA2-CAR. These engineered cells may be activated and expanded in vitro or in vivo. In a cellular therapy these engineered cells are infused to a recipient in need thereof. These cells may be a pharmaceutical composition (said cell plus pharmaceutical acceptable carrier). The infused cells are able to kill (or at least stop growth of) cancerous cells expressing BDCA2 in the recipient. The recipient may be the same subject from which the cells was obtained (autologous cell therapy) or may be from another subject of the same species.

In one embodiment of the invention the immune cells expressing the CAR specific for BDCA2 (BDCA2-CAR expressing cells) are applied to a subject suffering from cancer as cellular therapy as disclosed above but in combination with a second activating CAR, which is also expressed on the same engineered cells, recognizing an additional epitope to increase the specificity of the engineered cells expressing both CARs.

In one embodiment of the invention the BDCA2-CAR expressing cells are applied to a subject suffering from cancer as cellular therapy as disclosed above but in combination with a second, inhibitory CAR, which is also expressed on the same engineered cells, recognizing an additional epitope to increase the specificity of the engineered cells expressing both CARs.

The immune cells, preferentially T cells or NK cells engineered to express BDCA2-CAR may be administered either alone, or as a pharmaceutical composition in combination with diluents and/or with other components such as IL-2 or other cytokines or cell populations. Briefly, pharmaceutical compositions of the present invention may comprise a cell population of genetically modified cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease. A pharmaceutical composition comprising the immune cells, preferentially T cells or NK cells as disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected directly into a tumor, lymph node, or site of infection.

The cells may be activated and expanded to therapeutic effective amounts using methods known in the art.

The cells of the invention may be used in combination with e.g. chemotherapy, radiation, immunosuppressive agents, antibodies or antibody therapies.

In another embodiment, the CAR system (composition comprising the CAR specific for a tag of a tagged polypeptide ("anti-tag CAR") and said polypeptide specifically binding to BDCA2 as disclosed herein) may be for use in the treatment in a subject suffering from cancer. Cells such as immune cells, e.g. T cells or NK cells of a subject, may be isolated or established immune cell lines may be used. The subject may suffer from said cancer (a patient) or may be a healthy subject. These immune cells are genetically modified in vitro to express the CAR specific for a tag of a tagged polypeptide as disclosed herein. These engineered cells may be activated and expanded in vitro to a therapeutically effective population of expressing cells. In cellular therapy these engineered cells may be infused to a recipient in need thereof as a pharmaceutical composition (or a formulation of a therapeutically effective population of anti-tag CAR expressing cells), in addition to a second pharmaceutical composition, a formulation of the tagged polypeptide as disclosed herein. The infused cells in the recipient may be able to kill (or at least stop growth of) cancerous cells expressing the antigen which is recognized by the CAR system as disclosed herein. The recipient may be the same subject from which the cells were obtained (autologous cell therapy) or may be from another subject of the same species (allogeneic cell therapy).

The therapeutically effective population of anti-tag CAR expressing cells may be administered to the patient before the administration of the formulation of the tagged polypeptide to the subject. Alternatively, the formulation of the tagged polypeptide may be administered to the subject before or at the same time as the administration the therapeutically effective population of anti-tag CAR expressing cells to the subject. A further variation includes in-vitro culturing the therapeutically effective population of anti-LLE CAR expressing cells with the tagged polypeptide of the formulation of the tagged polypeptide prior to administration to the subject.

Populations of anti-tag-CAR-expressing (immune) cells may be formulated for administered to a subject using techniques known to the skilled artisan.

Formulations comprising therapeutically effective population(s) of anti-tag expressing CAR cells may include pharmaceutically acceptable excipient(s) (carrier or diluents). Excipients included in the formulations will have different purposes depending, for example, on the nature of the tag-binding domain of the anti-tag-CAR, the (sub) population of immune cells used, and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of a therapeutically effective population(s) of anti-tag expressing CAR cells may include one population of anti-tag CAR-expressing (immune) cells, or more than one population of anti-tag-CAR-expressing (immune) cells. The different populations of anti-tag-CAR (immune) cells may vary based on the identity of the tag-binding domain, the identity of the activation domain, the identity of the (sub)population of immune cells, or a combination thereof.

The formulations comprising therapeutically effective population(s) of anti-tag expressing CAR cells may be administered to a subject using modes and techniques known to the skilled artisan. Exemplary modes include, but are not limited to, intravenous injection. Other modes include, without limitation, intratumoral, intradermal, subcutaneous (s.c, s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

The formulations comprising therapeutically effective population(s) of anti-tag expressing CAR cells that are administered to a subject comprise a number of anti-tag-CAR-expressing cells such immune cells that is effective for the treatment of the specific indication or disorder. In general, formulations may be administered that comprise between about $1\times10^4$ and about $1\times10^{10}$ anti-tag-CAR-expressing cells such as immune cells. In most cases, the formulation may comprise between about $1\times10^5$ and about $1\times10^9$ anti-tag-CAR-expressing cells such as immune cells, from about $5\times10^5$ to about $5\times10^8$ anti-tag-CAR-expressing cells such as immune cells, or from about $1\times10^6$ to about $1\times10^7$ anti-tag-CAR -expressing cells such as immune cells. However, the number of anti-tag-CAR-expressing cells such as immune cells administered to a subject may vary between wide limits, depending upon the location, source, identity, extent and severity of the disorder, the age and condition of the individual to be treated, etc. A physician may ultimately determine appropriate dosages to be used.

The tagged polypeptides as disclosed herein may be formulated for administered to a subject using techniques known to the skilled artisan. Formulations of the tagged polypeptides may include pharmaceutically acceptable excipient(s) (carriers or diluents). Excipients included in the formulations will have different purposes depending, for example, on the nature of the tag, the antigen binding domain of the tagged polypeptide, and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of tagged polypeptide may include one type of tag polypeptide, or more than one type of tagged polypeptides. The different types of tagged polypeptides may vary based on the identity of the tag, the antigen binding moiety of the tagged polypeptode, or a combination thereof.

The tagged polypeptides may be administered to a subject using modes and techniques known to the skilled artisan. Exemplary modes include, but are not limited to, intravenous, intraperitoneal, and intratumoral injection. Other modes include, without limitation, intradermal, subcutaneous (s.c, s.q., sub-Q, Hypo), intramuscular (i.m.), intraarterial, intramedulary, intracardiac, intra-articular (joint), intrasynovial (joint fluid area), intracranial, intraspinal, and intrathecal (spinal fluids).

Formulations comprising the polypeptide are administered to a subject in an amount which is effective for treating the specific indication or disorder. In general, formulations comprising at least about 1 µg/kg to about 100 mg/kg body weight of the tagged polypeptide may be administered to a subject in need of treatment. In most cases, the dosage may be from about 100 µg/kg to about 10 mg/kg body weight of the tagged polypeptide daily, taking into account the routes of administration, symptoms, etc. The amount of tagged polypeptide in formulations administered to a subject may vary between wide limits, depending upon the location, source, identity, extent and severity of the disorder, the age and condition of the individual to be treated, etc. A physician may ultimately determine appropriate dosages to be used.

The timing between the administration of the CAR expressing cell formulation and the tag polypeptide-formulation may range widely depending on factors that include the type of (immune) cells being used, the binding specificity of the CAR, the identity of the tag, the antigen binding moiety of the tagged polypeptide, the identity of the target cell, e.g. cancer cell to be treated, the location of the target cell in the subject, the means used to administer the formulations to the subject, and the health, age and weight of the subject being treated. Indeed, the tagged polypeptide formulation may be administered prior to, simultaneous with, or after the genetically engineered (immune) cell formulation.

Depending on the disorder being treatment the step of administering the CAR expressing cell formulation, or the step of administering the tagged polypeptide formulation, or both, can be repeated one or more times. When two or more formulations of tagged polypeptides may be applied to a subject, the formulations applied may comprise the same or different tagged polypeptides. When two or more formulations of engineered cells such as immune cells expressing the CAR of the invention are applied to a subject, the engineered cells may be of the same cell type or of different cell types, e.g. T cells and/or NK cells. A formulation of cells such as immune cells may also comprise more than one cell type, each expressing the CAR of the invention.

All definitions, characteristics and embodiments defined herein with regard to the first aspect of the invention as disclosed herein also apply mutatis mutandis in the context of the other aspects of the invention as disclosed herein.

In addition to above described applications and embodiments of the invention further embodiments of the invention are described in the following without intention to be limited to these embodiments.

Embodiments

The present invention also encompasses nucleic acids (DNA or RNA) constructs comprising sequences encoding for amino acids sequences of a CAR specific for BDCA2 such as SEQ ID NO:1 and SEQ ID NO:2.

In one embodiment of the invention a DNA construct (vector, plasmid) is generated encoding for a CAR specific for BDCA2. A nucleic acid sequence encoding for an antigen binding domain specific for BDCA2 is fused at least to a nucleic acid sequence encoding a transmembrane domain and subsequent a nucleic acid sequence encoding an intracellular domain. The construction of such expression vectors can be performed by recombinant methods well known in the art. Alternatively, the nucleic acid sequences can be produced synthetically.

In one embodiment of the invention a cell expressing the CAR of the invention is generated. The DNA construct encoding the CAR of the invention can be transfected or transduced into a host cell by methods well known in the art (e.g. viral-based systems, physical methods, biological methods, chemical methods). Regardless the methods used to integrate, preferentially stably integrate, the nucleic acid encoding the CAR of the invention, in the host cell, as a result the host cell expresses a CAR which is specific for BDCA2.

In one embodiment of the invention the CAR specific for the antigen BDCA2 is expressed in immune cells or immune cell subsets.

In one embodiment of the invention the CAR specific for the antigen BDCA2 is expressed in T cells or T cell subsets.

In one embodiment of the invention the CAR specific for the antigen BDCA2 is expressed in NK cells or NK cell subsets.

In one embodiment of the invention an engineered cell expressing a CAR specific for BDCA2 (the "BDCA2-CAR") is isolated (enriched or separated) after the transfection/transduction process for generating such an engineered BDCA2-CAR cell from non-transfected/transduced cells by methods well known in the art, e.g. fluorescent based separating technologies such as FACS® or magnetic cell separation methods such as MACS®.

In an embodiment of the invention a source of immune cells, preferentially T cells or NK cells is obtained from a subject. Immune cells, preferentially T cells or NK cells can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FCASsort) or magnetic sorting (e.g. MACS®).

In one embodiment T cells of a blood sample of a subject are magnetically labelled, for example with a magnetic bead coupled to antibodies specific for CD4 and for CD8, respectively, washed, magnetically enriched and collected. Then these T cells may be engineered to express the BDCA2-CAR on their cell surface.

In one embodiment NK cells of a blood sample of a subject are magnetically labelled, for example with a magnetic bead coupled to antibodies specific for CD3 and for CD56, respectively, washed, magnetically deplete CD3$^+$ cells, enriched CD56$^+$ cells and collected. Then these NK cells may be engineered to express the BDCA2-CAR on their cell surface. In one embodiment NK cells of a blood sample of a subject are magnetically labelled, for example with a magnetic bead coupled to antibodies specific for CD56, washed, magnetically enriched CD56$^+$ cells and collected. Then these CD56$^+$ cells (NK cells) may be engineered to express the BDCA2-CAR on their cell surface.

In one embodiment of the invention the isolated/enriched engineered NK cells expressing BDCA2-CAR prior or after genetic modification can be activated and expanded to increase amount of engineered NK cells generally using methods well known in the art, for example different combination of IL-2, IL-15, IL-21 and IL-1 family of cytokines or feeder cell based expansion method. Preferentially, said amount of engineered NK cells is increased to a therapeutic effective amount.

In one embodiment of the invention the isolated/enriched engineered T cells expressing BDCA2-CAR prior or after genetic modification can be activated and expanded to increase amount of engineered T cells generally using methods well known in the art, for example polyclonal stimulation with anti-CD3/anti-CD28 beads or anti-CD3/anti-CD28 nanomatrices (EP2711418B1). Preferentially, said amount of engineered T cells is increased to a therapeutic effective amount.

In one embodiment of the invention a cell expressing the CAR of the invention is generated. The RNA encoding the CAR of the invention can be transfected or transduced into a host cell by methods well known in the art (e.g. viral-based systems, physical methods, biological methods, chemical methods). In general, such an "RNA-engineered cell" is disclosed in detail in WO2013/040557. Regardless the methods used to integrate the RNA encoding the CAR of the invention, in the host cell, as a result the host cell expresses a CAR which is specific for BDCA2. Using "RNA-engineered cells" lead to the fact that the CAR is expressed for a limited time in the cell (transient expression).

In one embodiment of the invention the genetically modified cells expressing BDCA2-CAR, preferentially NK, and T cells, are generated automatically in a closed cell culture system. A process for generation of genetically modified cells, preferentially NK and T cells, NK and T cell subsets or NK and T cell progenitors comprises the steps:
a) providing a cell sample
b) preparation of the cell sample by centrifugation
c) magnetic separation of the cell, preferentially NK and T cells, NK and T cell subsets or NK and T cell progenitors
d) activation of the enriched cells, preferentially NK and T cells, NK and T cell subsets or NK and T cell progenitors using modulatory agents
e) genetically modifying the cells, preferentially NK and T cells, NK and T cell subsets or NK and T cell progenitors to express BDCA2-CAR
f) expansion of the genetically modified NK and T cells, NK and T cell subsets or NK and T cell progenitors in a cultivation chamber
g) washing of the cultured cells, preferentially NK and T cells, NK and T cell subsets or NK and T cell progenitors.

All these steps may be performed in a closed and sterile system.

The process is especially suited for preparing gene modified cells, preferentially NK and T cells, NK and T cell subsets or NK and T cell progenitors wherein the enriched cells, preferentially NK and T cells, NK and T cell subsets or NK and T cell progenitors are gene modified by using viral and/or non-viral vectors.

Any of these steps may be multiplied, omitted or may occur in a different order.

In an embodiment of the invention, the modulatory agents are selected from agonistic antibodies and/or cytokines.

In an embodiment of the invention in said automated process, the gene-modified cells, preferentially NK and T cells, NK and T cell subsets or NK and T cell progenitors are enriched by magnetic labelling of cells and magnetic separation before or after cultivation to obtain higher frequency of gene-modified cells, preferentially NK and T cells, NK and T cell subsets or NK and T cell progenitors in the final cellular product.

As closed and sterile system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes. It has been developed to fully automate and standardize the manufacturing process of cellular therapeutic agents. The instrument can perform sample loading, cell washing, density-based cell separations including erythrocyte reduction and plasma harvesting, magnetic separation, cell activation, cell modification (transduction), cell culture, and final product formulation.

Thus enabling the flexible integration of process modules ("steps") in a closed, automated and safe GMP compliant workflow reproducing a complex desired biological process.

In one embodiment of the invention the BDCA2-CAR of the invention is used for treatment in a subject having a disease, disorder or condition associated with an abnormal expression of BDCA2.

In one embodiment of the invention the BDCA2-CAR of the invention is for use in treatment of cancer in a subject suffering from cancer, wherein the cancerous cells of said cancer expresses BDCA2. Immune cells, e.g. T cells or NK cells of a subject are isolated. The subject may suffer from said cancer or may be a healthy subject. These cells are genetically modified in vitro or in vivo to express BDCA2-CAR. These engineered cells may be activated and expanded in vitro or in vivo. In a cellular therapy these engineered cells are infused to a recipient in need thereof. These cells may be a pharmaceutical composition (said cell plus pharmaceutical acceptable carrier). The infused cells are able to kill (or at least stop growth of) cancerous cells expressing BDCA2 in the recipient. The recipient may be the same subject from which the cells was obtained (autologous cell therapy) or may be from another subject of the same species In one embodiment of the invention the BDCA2-CAR expressing cells are applied to a subject suffering from cancer as cellular therapy as disclosed above but in combination with a second activating CAR, which is also expressed on the same engineered cells, recognizing an additional epitope to increase the specificity of the engineered cells expressing both CARs. This epitope can be membrane bound, part of the extracellular matrix, or a soluble component.

In one embodiment of the invention the BDCA2-CAR expressing cells are applied to a subject suffering from cancer as cellular therapy as disclosed above but in combination with a second, inhibitory CAR, which is also expressed on the same engineered cells, recognizing an additional epitope to increase the specificity of the engineered cells expressing both CARs. This epitope can be membrane bound, part of the extracellular matrix, or a soluble component.

Definitions

Unless defined otherwise, technical and scientific terms used herein have the same meaning as commonly understood by one of ordinary skill in the art to which this invention belongs.

In general, a CAR as disclosed herein may comprise an extracellular domain (extracellular part) comprising the antigen binding domain, a transmembrane domain and a cytoplasmic signaling domain (intracellular signaling domain). The extracellular domain may be linked to the transmembrane domain by a linker or spacer. The extracellular domain may also comprise a signal peptide. In some embodiments of the invention the antigen binding domain of a CAR binds a tag or hapten that is coupled to a polypeptide ("haptenylated" or "tagged" polypeptide), wherein the polypeptide may bind to a disease-associated antigen such as a tumor associated antigen (TAA) that may be expressed on the surface of a cancer cell.

Such a CAR may be also named "anti-tag" CAR or "adapterCAR" or "universal CAR" as disclosed e.g. in US9233125B2.

The haptens or tags may be coupled directly or indirectly to a polypeptide (the tagged polypeptide), wherein the polypeptide may bind to said disease associated antigen expressed on the (cell) surface of a target, i.e. BDCA2. The tag may be e.g. a hapten such as biotin or fluorescein isothiocyanate (FITC) or phycoerythrin (PE), but the tag may also be a peptide sequence e.g. chemically or recombinantly coupled to the polypeptide part of the tagged polypeptide. The tag may also be streptavidin. The tag portion of the tagged polypeptide is only constrained by being a molecular that can be recognized and specifically bound by the antigen binding domain specific for the tag of the CAR. For example, when the tag is FITC (Fluorescein isothiocyanate), the tag-binding domain may constitute an anti-FITC scFv. Alternatively, when the tag is biotin or PE (phycoerythrin), the tag-binding domain may constitute an anti-biotin scFv or an anti-PE scFv.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen, e.g. to a tumor associated antigen (TAA) or tumor specific antigen (TSA) or the tag of a tagged polypeptide. The CARs of the invention may comprise one or more antigen binding domains (e.g. a tandem CAR). Generally, the targeting regions on the CAR are extracellular. The antigen binding domain may comprise an antibody or an antigen binding fragment thereof. The antigen binding domain may comprise, for example, immunoglobulin full length heavy and/or light chains, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G_4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge. The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (e.g. WO2014127261A1) due to small molecule-dependent heterodimerizing domains in each polypeptide of the CAR.

The cytoplasmic signaling domain (or the intracellular signaling domain) of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ (CD3zeta).

The cytoplasmic domain of the CAR may be designed to comprise the CD3ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD137. In a further example, the cytoplasmic domain may comprise the signaling domain of CD3ζ, the signaling domain of CD28, and the signaling domain of CD137.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR expressing immune cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD).

In some embodiments, the endodomain may contain a primary cytoplasmic signaling domain or a co-stimulatory region, but not both. In these embodiments, an immune effector cell containing the disclosed CAR is only activated if another CAR containing the missing domain also binds its respective antigen.

In some embodiment of the invention the CAR may be a "SUPRA" (split, universal, and programmable) CAR, where a "zipCAR" domain may link an intra-cellular costimulatory domain and an extracellular leucine zipper (WO2017/091546). This zipper may be targeted with a complementary zipper fused e.g. to an scFv region to render the SUPRA CAR T cell tumor specific. This approach would be particularly useful for generating universal CAR T cells for various tumors; adaptor molecules could be designed for tumor specificity and would provide options for altering specificity post-adoptive transfer, key for situations of selection pressure and antigen escape.

The CARs of the present invention may be designed to comprise any portion or part of the above-mentioned domains as described herein in any order and/or combination resulting in a functional CAR, i.e. a CAR that mediated an immune effector response of the immune effector cell that expresses the CAR as disclosed herein.

The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The antigen BDCA2 (also named CLEC4C) is a membrane protein of plasmacytoid dendritic cells used as a marker for this kind of cells and denoted as CD303 in the nomenclature of the Cluster of differentiation. Preferentially the BDCA2 antigen as used herein is a human BDCA2 antigen.

The term "autologous" as used herein refers to any material derived from the same subject to who it is later re-introduced.

The term "allogeneic" as used herein refers to any material derived from a different subject of the same species as the subject to who the material is re-introduced.

The term "isolated" means altered or removed from the natural state. For example an isolated population of cells means an enrichment of such cells and separation from other cells which are normally associated in their naturally occurring state with said isolated cells. An isolated population of cells means a population of substantially purified cells which are a homogenous population of cells.

The terms "specifically binds" or "specific for" with respect to an antigen-binding domain of an antibody, of a fragment thereof or of a CAR refer to an antigen-binding domain which recognizes and binds to a specific antigen, i.e. BDCA2, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells or NK cells can be manipulated by recombinant methods well known in the art to express stably or transiently peptides or proteins which are not expressed in these cells in the natural state. For example T cells or NK cells, preferentially human T cells or NK cells are engineered to express an artificial construct such as a chimeric antigen receptor on their cell surface. For example, the CAR sequences may be delivered into cells using a retroviral or lentiviral vector.

The amino acid sequences of BDCA2 $V_L$ and BDCA2 $V_H$, are given in SEQ ID NO:1 and SEQ ID NO:2, and linked via a linker in SEQ ID NO:4, respectively. The amino acid sequences (proteins, polypeptides) as given in the SEQ ID NO1 to SEQ ID NO:4 refer to all constellations of the respective amino acid sequence which retains the intended function of the respective amino acid sequence as defined herein. In other words, the divergences to the SEQ ID No:1, SEQ ID NO:2, and SEQ ID NO:4, respectively, should not affect their potential as binding specifically to the antigen BDCA2 and/or being a functional CAR. Therefore, the amino acid sequences of SEQ ID NO:1 to SEQ ID NO:4 can be the full length amino acid sequence of the SEQ ID NO:1 to SEQ ID NO:4, respectively. It can also be a variant thereof which have some amino acids deleted, added or replaced while still retaining the intended function as described herein. Therefore, included in this definition are variants of the amino acid sequences in SEQ ID NO: 1 to SEQ ID NO:4, respectively, such as amino acid sequences essentially similar to SEQ ID NO: 1 to SEQ ID NO:4, respectively, having a sequence identity of at least 70%, or at least 75%, 80%, 85%, 90%, 95%, 97%, 98% or 99% at the amino acid sequence level. In the context of the present invention, "sequence identity" may be determined using pairwise alignments using alignments programs for amino acid sequences well known to the art.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as $CD4^+$ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, Th9, or $T_{FH}$, which secrete different cytokines to facilitate a different type of immune response. Signaling from the APC directs T cells into particular subtypes.

Cytotoxic T cells ($T_c$ cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells ($T_{CM}$ cells) and two types of effector memory T cells (TEM cells and TEMRA cells). Memory cells may be either $CD4^+$ or $CD8^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of $CD4^+$ $T_{reg}$ cells have been described—Foxp3+$T_{reg}$ cells and Foxp3−$T_{reg}$ cells.

Natural killer T cells (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both $T_h$ and $T_c$ cells (i.e., cytokine production and release of cytolytic/cell killing molecules).

The term "natural killer cells (NK cells)" are defined as large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8. Continuously growing NK cell lines can be established from cancer patients and common NK cell lines are for instance NK-92, NKL and YTS.

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based or NK cell-based cytotoxic responses to attack cancer cells. T cells that have a natural or genetically engineered reactivity to a patient's cancer are generated in vitro and then transferred back into the cancer patient.

The term "treatment" as used herein means to reduce the frequency or severity of at least one sign or symptom of a disease.

The term "biomarker" or "marker" is widespread in the art and may broadly denote a biological molecule and/or a detectable portion thereof (e.g. a nucleic acid, a peptide or a lipid such as a glyco lipid) whose qualitative and/or quantitative evaluation in an individual is predictive or informative (e.g., predictive, diagnostic and/or prognostic) with respect to one or more aspects of the individual's phenotype and/or genotype, such as, for example, with respect to the status of the individual. E.g. the biomarker is predictive or informative with respect to the outcome for chemotherapeutic treatment of a cancer in an individual. A biomarker is expressed ("expression of the biomarker") if the biomarker is detectable with methods known in the art.

Therefore expression of biomarkers encompasses not only expression at nucleic acid level (DNA and/or RNA) and protein level but also expression (presence) of other biological structures on or in the cells such as glycolipids or the activity of a protein.

As used herein, the term "subject" refer to an animal. Preferentially, the subject is a mammal such as mouse, rat, cow, pig, goat, chicken dog, monkey or human. More preferentially, the individual is a human. The subject may be a subject suffering from a disease such as cancer (a patient), but the subject may be also a healthy subject.

The term "target" as used herein refers to an antigen or epitope associated with a cell that should be recognized specifically by an antigen binding domain, e.g. an antigen binding domain of an antibody or of a CAR. The antigen or epitope can be bound to the cell surface but also be secreted, part of the extracellular membrane, or shed from the cell.

The term "antibody" as used herein refers to polyclonal or monoclonal antibodies and antigen binding fragments thereof, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The terms "immune cell" or "immune effector cell" refer to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, mesenchymal stem cells or mesenchymal stromal cells (MSC), monocytes or macrophages. Preferentially these immune cells are human immune cells. Preferred immune cells are cells with cytotoxic effector function such as alpha-beta T cells, NK cells, NKT cells, ILC, CIK cells, LAK cells or gamma-delta T cells. Most preferred immune effector cells are T cells and NK cells. "Effector function" means a specialized function of a cell, e.g. in a T cell an effector function may be cytolytic activity or helper activity including the secretion of cytokines.

The term "tagged polypeptide" as used herein refers to a polypeptide that has bound thereto directly or indirectly at least one additional component, i.e. the tag. The polypeptide may be an antibody or antigen binding fragment thereof that binds to an antigen expressed on the surface of a target cell such as a tumor associated antigen on a cancer cell. The tag may be a hapten such as FITC, biotin, PE, or streptavidin and the hapten may be bound by the anti-hapten (anti-tag) binding domain of the CAR.

Haptens are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

Alternatively, the tag may also be a peptide sequence e.g. chemically or recombinantly coupled to the polypeptide part of the tagged polypeptide. Tags for "anti-tagCAR systems" are well known in the art and any tag suitable for such a system of anti-tagCAR and tagged polypeptide may be used herein.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The tumor associated antigen (TAA) as used herein refers to an antigenic substance produced in tumor cells. Tumor associated antigens are useful tumor or cancer markers in identifying tumor/cancer cells with diagnostic tests and are potential candidates for use in cancer therapy. Preferentially, the TAA may be expressed on the cell surface of the tumor/cancer cell, so that it may be recognized by the antigen binding receptor as disclosed herein.

The term "target cell" as used herein refers to cell which expresses an antigen on its cell surface that should be recognized (bound) by the antigen binding domain of the CAR as disclosed herein or by the antigen binding domain of the tag of the tagged polypeptide as disclosed herein.

As used herein, the term "subject" refers to a mammal such as mouse, rat, cow, pig, goat, chicken dog, monkey or human. Preferentially, the subject is a human. The subject may be a subject suffering from a disorder such as cancer (a patient), but the subject may be also a healthy subject.

The terms "therapeutically effective amount" or "therapeutically effective population" mean an amount of a cell population which provides a therapeutic benefit in a subject.

The terms "specifically binds" or "specific for" with respect to an antigen binding domain of an antibody, of an antigen binding fragment thereof, as used e.g. in the CAR as disclosed herein, or in the tagged polypeptide refer to an antigen binding domain which recognizes and binds to a specific antigen, but does not substantially recognize or bind other molecules in a sample. An antigen binding domain that binds specifically to an antigen from one species may bind also to that antigen from another species. This cross-species reactivity is typical to many antibodies and therefore not contrary to the definition of that antigen binding domain as specific. An antigen binding domain that specifically binds to an antigen may bind also to different allelic forms of the antigen (allelic variants, splice variants, isoforms etc.) or homologous variants of this antigen from the same gene family. This cross reactivity is typical to many antibodies and therefore not contrary to the definition of that antigen binding domain as specific.

The term "isolated" means altered or removed from the natural state. For example an isolated population of cells means an enrichment of such cells and separation from other cells which are normally associated in their naturally occurring state with said isolated cells. An isolated population of cells means a population of substantially purified cells which are a homogenous population of cells.

The term "expression" as used herein is defined as the transcription and/or translation of a particular nucleotide sequence driven by its promoter in a cell.

EXAMPLES

Example 1

Generation of NK and T Cells Expressing BDCA2 CAR

Figure 1:
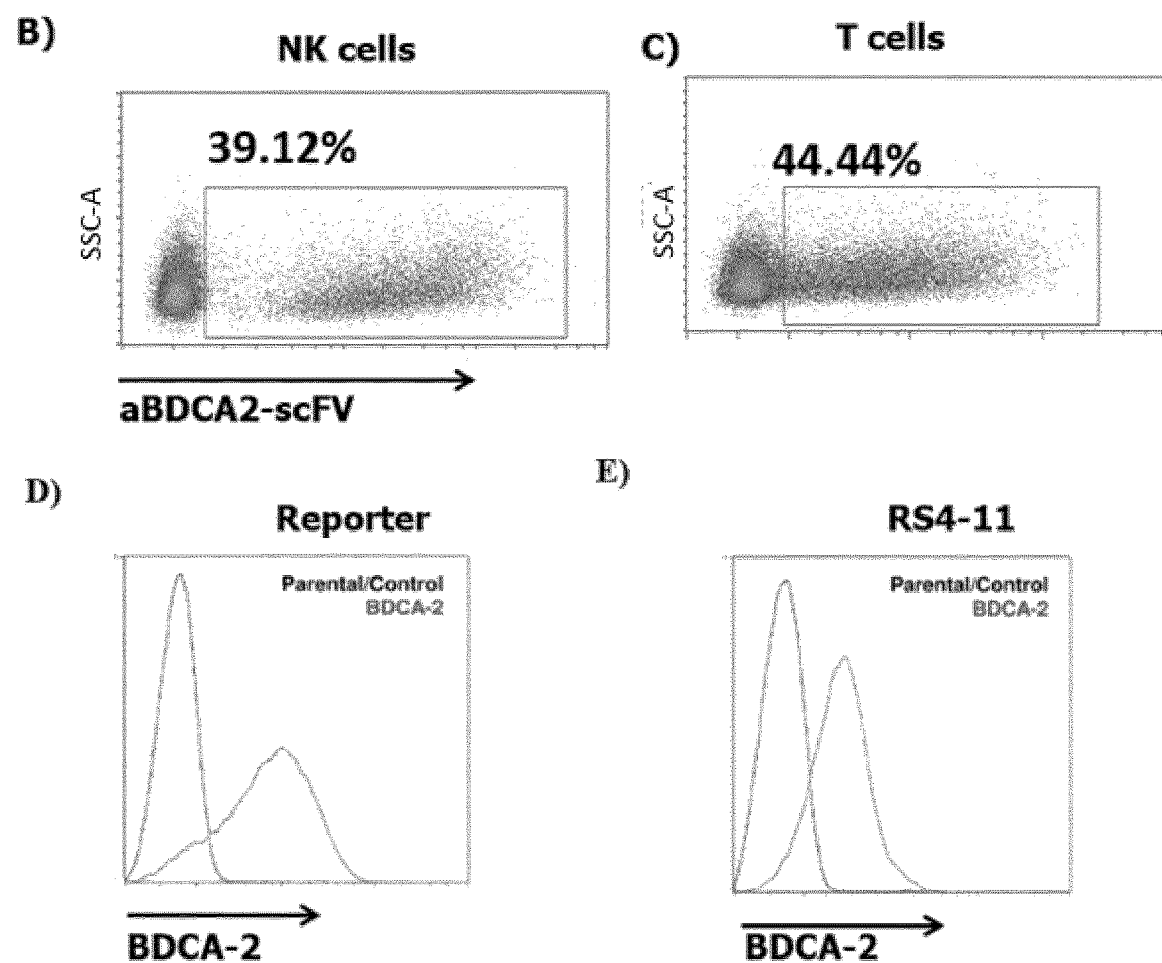
FIG. 1: Design of BDCA2 CAR construct and expression in NK and T cells.

We have cloned aBDCA2-scFV into lentiviral vector backbone and generated high-titer lentiviral vectors (LVs). Primary NK and T cells were isolated from donor peripheral blood mononuclear cells (PBMCs). NK cells were cultured in NK cell medium (Miltenyi Biotec) containing IL-2 and IL-15 for 2 days. On day 2, we transduced the pre-activated NK and T cells with lentiviral vectors containing aBDCA2-scFV. We determined the CAR expression with specific idiotype against aBDCA2-scFV on day 8 (FIG. 1B and 1C). The BDCA2 CAR expressed by these cells comprise the BDCA2 binding domains of SEQ ID NO:1 and SEQ ID NO:2 in the order from the N-terminus to the C-terminus: SEQ ID NO:1 followed by SEQ ID NO:2.

NK cells have natural cytotoxicity against many cell lines. We found two cell lines (human RS411 and mouse A95-KK) that are resistance to natural killing of NK cell thus representing a good choice as a target for engineered CAR-NK and CAR-T cells. RS411 is a pre B cell line purchased from ATCC and reporter is a mouse T cell hybridoma (A95-KK) cell line received from Miltenyi GmbH, Germany. Both cell lines were transduced with BDCA2 and stable cell line expressing BDCA2 were generated (FIG. 1D, reporter and 2E, RS4-11).

Example 2

Cytotoxicity of BDCA2-CAR Transduced Effector Cells

Figure 2:
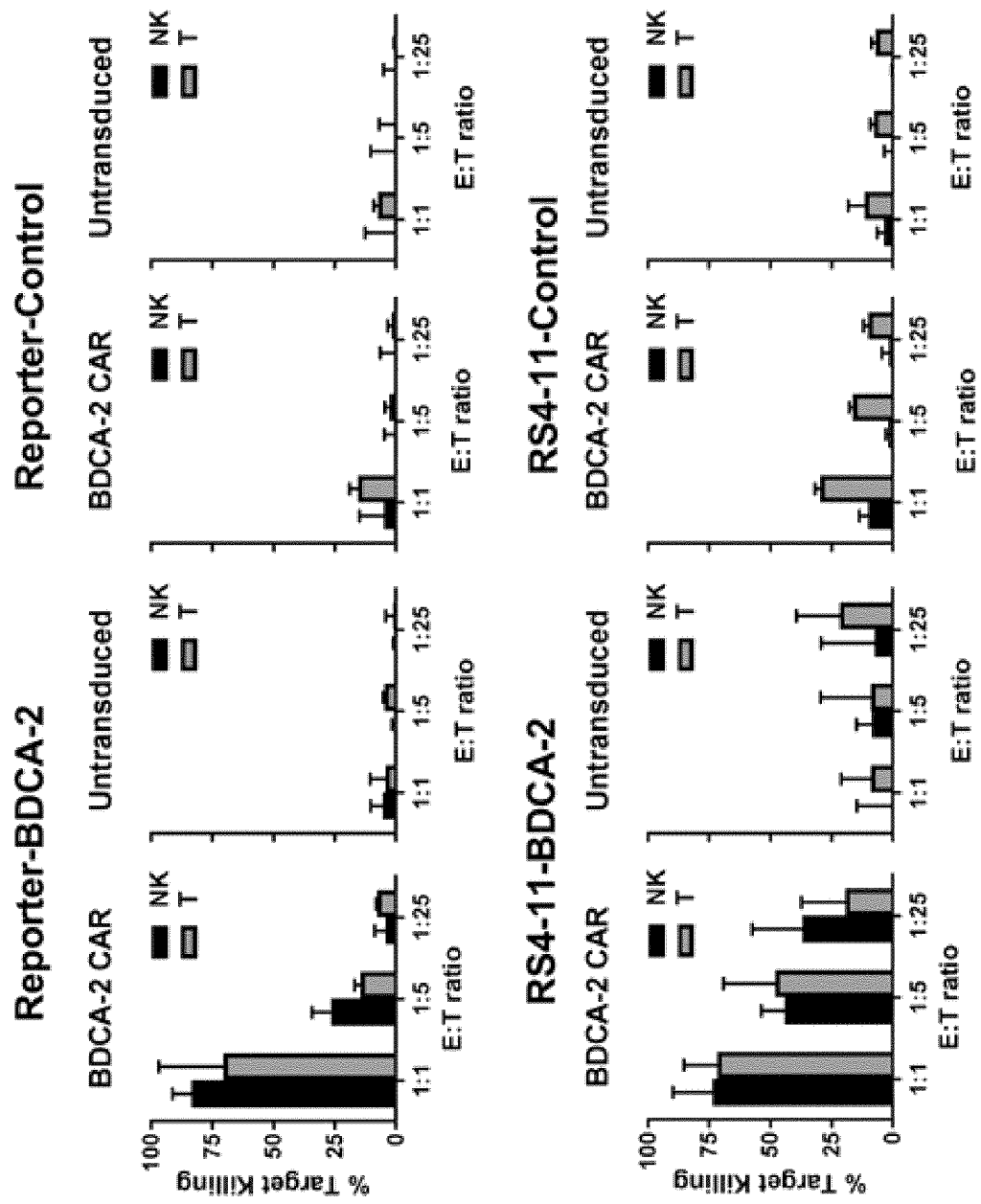
FIG. 2: CAR-NK and CAR-T cells specifically kill target cells expressing BDCA2.

The specific cytotoxicity of BDCA2-CAR was determined by flow cytometry based cytotoxic assay (Granzin M, et al., Cytotherapy. 2015). Activated NK and T cells without CAR-BDCA2 showed little killing (<10% killing) against target cells expressing BDCA2 (FIG. 2). However, engineered T-cells showed slightly higher background killing of non-transduced target cells (Reporter-Control and RS4-11-control, non-transduced). Both effector cells expressing BDCA2-CAR are highly cytotoxic (>70% killing at E:T=1:1) against target cells expressing BDCA2 (FIG. 2, reporter-BDCA2 and RS4-11-BDCA2, upper and lower panel, respectively). Surprisingly, these target cell lines are highly resistant to the natural killing of non-engineered NK cells, suggesting that the engineered CAR-NK cells can overcome the natural resistance of cancer cells. CAR-NK cells showed slightly higher killing of target cells than CAR-T cells despite having lower expression of aBDCA2 CAR (FIG. 2).

Example 3

Cytokines Production of BDCA2-CAR NK and BDCA2-CAR T Cells

We analyzed the cytokines production of BDCA2-CAR-NK and BDCA2-CAR-T cells in the presence of target cells using MACSPlex cytokine kits from Miltenyi Biotec. BDCA2-CAR-NK cells produced very low or undetectable amounts of IFN-gamma and TNF-alpha after co-culturing with target cells without BDCA2 but produce higher amount of cytokines when co-culture with BDCA2 expressing target cells. (FIG. 3, RS4-11 NK and Reporter NK). On the other hand, BDCA2-CAR-T cells produced about 100-fold higher amount of cytokines than NK cells when co-culturing them with target cells expressing BDCA2 (FIG. 3). Surprisingly, BDCA2-CAR-T cells produce significant amount of cytokines even when co-culturing them with target cells without BDCA2.

Example 4

The Phenotypical Characteristics of Non-Transduced and BDCA2-CAR Transduced NK Cells.

To understand any changes in the phenotype of NK cells upon BDCA2-CAR transduction, we compared the expression of common NK cell markers between non-transduced and transduced NK cells. Primary NK cells were isolated from PBMC using NK cell isolation kits from Miltenyi Biotec following the instruction of manufacturer. The cells were culture in NKMACS medium (Miltenyi Biotec) containing IL-2 and IL-15. On day 2, the NK cells were transduced with BDCA2-CAR as described before. Non-transduced NK cells were treated and culture in same condition as transduced NK cells and used as control. On day 8 after transduction, both transduced and non-transduced cells were washed, counted and stained with monoclonal antibody against different NK cells receptors, and expressions were determined using flow cytometry. The expression of commonly known NK cell markers in non-transduced and transduced NK cells are similar (FIG. 6) suggesting that there is no phenotypic abnormality in NK cells after transduced with BDCA2-CAR.

Example 5

Effect of BDCA2-CAR on Cellular Metabolism of NK Cells.

It is known that the cellular metabolism is significantly different in CD19 CAR transduced T cells compared to non-transduced T cells (Kawalekar O U et al., 2016). To understand the interconnection of cellular metabolism and CAR signaling in NK cells, we compared the metabolic profiles of NK cells transduced with BDCA2-CAR with non-transduced NK cells using an extracellular flux analyzer (seahorse, Agilent) following manufacturer instructions. We measured the oxygen consumption rate (OCR) of non-transduced and BDCA2-CAR transduced NK cells 8 days after transduction. Basal OCR was measured, followed by serial additions of oligomycin (an inhibitor of ATP synthesis), carbonyl cyanide-ptrifluoromethoxyphenylhydrazone (FCCP; an uncoupling ionophore), and rotenone with antimycin A (blocking agents for complexes I and III of the electron transport chain, respectively) to discern the relative contributions of mitochondrial and non-mitochondrial mechanism of oxygen consumption. The basal OCR profiles were similar between non-transduced and BDCA2-CAR transduced NK cells as expected (FIG. 5, FIG. 6A). We could not find significant difference in maximal respiration between the two group although CAR transduced NK cells seem to have little higher respiration 8 days after the transduction (FIG. 6B). We have also measured the extracellular acidification rate (ECAR) of non-transduced and transduced NK cells and found them similar (FIG. 6C). Together, these results suggest, unlike T cells, NK cells showed no changes in their metabolic activity upon transduced with CAR.

References:

1. Vardiman J W, Thiele J, Arber D A, Brunning R D, Borowitz M J, Porwit A, Harris N L, Le Beau M M, Hellström-Lindberg E, Tefferi A, Bloomfield C D. The 2008 revision of the World Health Organization (WHO) classification of myeloid neoplasms and acute leukemia: rationale and important changes. Blood. 2009 Jul 30;114(5):937-51

2. Taylor J, Kim S S, Stevenson K E, et al. Loss-of-function mutations in the splicing factor ZRSR2 are common in blastic plasmacytoid dendritic cell neoplasm and have male predominance [ASH abstract 741]. *Blood.* 2013;1 22(21)(suppl)

3. Roos-Weil D, Dietrich S, Boumendil A, et al; European Group for Blood and Marrow Transplantation Lymphoma, Pediatric Diseases, and Acute Leukemia Working Parties.

Stem cell transplantation can provide durable disease control in blastic plasmacytoid dendritic cell neoplasm: a retrospective study from the European Group for Blood and Marrow Transplantation. *Blood.* 2013;121(3):440-446.

4. Sadelain M, Rivière I, Riddell S. Therapeutic T cell engineering. Nature. 2017 May 24;545(7655):423-431. doi: 10.1038/nature22395.

5. Boiocchi L, Lonardi S, Vermi W, Fisogni S, Facchetti F. BDCA-2 (CD303): a highly specific marker for normal and neoplastic plasmacytoid dendritic cells. Blood. 2013 Jul 11;122(2):296-7. doi: 10.1182/blood-2013-05-500413.

6. Granzin M, Soltenborn S, Müller S, Kollet J, Berg M, Cerwenka A, Childs R W, Huppert V. Fully automated expansion and activation of clinical-grade natural killer cells for adoptive immunotherapy. Cytotherapy. 2015 May;17(5): 621-32.

7. Kawalekar O U, O'Connor R S, Fraietta J A, Guo L, McGettigan S E, Posey A D Jr, Patel P R, Guedan S, Scholler J, Keith B, Snyder N W, Blair I A, Milone M C, June C H. Distinct Signaling of Coreceptors Regulates Specific Metabolism Pathways and Impacts Memory Development in CAR T Cells. Immunity. 2016 Feb 16;44(2):380-90

The invention claimed is:

1. A chimeric antigen receptor (CAR) comprising an antigen binding domain specific for BDCA2, a transmembrane domain and an intracellular signaling domain comprising a primary signaling domain, wherein said antigen binding domain comprises the amino acid sequences of SEQ ID NO:1 and SEQ ID NO: 2.

2. The CAR according to claim 1, wherein the CAR comprises the amino acid sequence SEQ ID NO:4.

3. An isolated population of engineered immune cells comprising a nucleic acid sequence that encodes a CAR comprising an antigen binding domain specific for BDCA2, a transmembrane domain and an intracellular signaling domain comprising a primary signaling domain, wherein said antigen binding domain comprises comprising the amino acid sequences of SEQ ID NO: 1 and SEQ ID NO: 2.

4. An isolated population of engineered NK cells comprising a nucleic acid sequence that encodes a chimeric antigen receptor (CAR) comprising an antigen binding domain specific for BDCA2 comprising, wherein said antigen binding domain comprises the amino acid sequences of SEQ ID NO: 1 and SEQ ID NO: 2, a transmembrane domain and an intracellular signaling domain comprising a primary signaling domain.

5. A composition comprising:
a) an immune cell expressing a CAR comprising:
i) an antigen binding domain specific for a tag of a tagged polypeptide, wherein said tagged polypeptide is an antibody or antigen binding fragment thereof comprising the amino acid sequence of SEQ ID NO: 1 and SEQ ID NO: 2,
ii) a transmembrane domain,
iii) an intracellular signaling domain, and
wherein said antigen binding domain specifically binds a tag of a tagged polypeptide, wherein said polypeptide binds specifically to the antigen BDCA2 expressed on the surface of a target cell, wherein said target cell is a cancer cell expressing BDCA2, and
b) said tagged polypeptide.

6. The composition according to claim 5, wherein said tagged polypeptide is an antibody or antigen binding fragment thereof comprising the amino acid sequence of SEQ ID NO:4.

7. The composition according to claim 5, wherein said immune cell is an NK cell.

* * * * *

UNITED STATES PATENT AND TRADEMARK OFFICE
CERTIFICATE OF CORRECTION

PATENT NO. : 11,701,387 B2
APPLICATION NO. : 16/959330
DATED : July 18, 2023
INVENTOR(S) : Rafijul Bari et al.

It is certified that error appears in the above-identified patent and that said Letters Patent is hereby corrected as shown below:

In the Claims

Column 27
Line 14, in Claim 3, after "comprises" delete "comprising"
Line 19, in Claim 4, delete "BDCA2 comprising," and insert -- BDCA2, --

Signed and Sealed this
Twelfth Day of September, 2023

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 107
<212> TYPE: PRT
<213> ORGANISM: Artificial sequence
<220> FEATURE:
<223> OTHER INFORMATION: BDCA2-scFV heavy chain

<400> SEQUENCE: 1

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Thr Asp Phe Thr Leu Thr Ile Ser Ser Leu Gln Ser
65                  70                  75                  80

Glu Asp Phe Ala Thr Tyr Tyr Cys Leu Gln Tyr Ala Ser Tyr Pro Pro
                85                  90                  95

Thr Phe Gly Gly Gly Thr Lys Leu Glu Ile Lys
            100                 105

<210> SEQ ID NO 2
<211> LENGTH: 119
<212> TYPE: PRT
<213> ORGANISM: Artificial sequence
<220> FEATURE:
<223> OTHER INFORMATION: BDCA2-scFV light chain

<400> SEQUENCE: 2

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Glu Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr Arg Asn Trp Asp Tyr Tyr Thr Met Asp Tyr Trp Gly Gln Gly
            100                 105                 110
```

```
Thr Thr Val Thr Val Ser Ser
        115

<210> SEQ ID NO 3
<211> LENGTH: 15
<212> TYPE: PRT
<213> ORGANISM: Artificial sequence
<220> FEATURE:
<223> OTHER INFORMATION: Linker

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 241
<212> TYPE: PRT
<213> ORGANISM: Artificial sequence
<220> FEATURE:
<223> OTHER INFORMATION: Complete BDCA2-scFV

<400> SEQUENCE: 4

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Glu Ile Ser Gly Tyr
                20                  25                  30

Leu Ser Trp Tyr Gln Gln Lys Pro Gly Lys Ala Ile Lys Arg Leu Ile
            35                  40                  45

Tyr Ala Ala Ser Thr Leu Asp Ser Gly Val Pro Ser Arg Phe Ser Gly
        50                  55                  60

Ser Arg Ser Gly Thr Asp Phe Thr Leu Thr Ile Ser Ser Leu Gln Ser
65                  70                  75                  80

Glu Asp Phe Ala Thr Tyr Tyr Cys Leu Gln Tyr Ala Ser Tyr Pro Pro
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Gly Ser Gln Val Thr Leu Lys Glu
            115                 120                 125

Ser Gly Pro Thr Leu Val Lys Pro Thr Gln Thr Leu Thr Leu Thr Cys
        130                 135                 140

Thr Phe Ser Gly Phe Ser Leu Ser Thr Ser Gly Met Gly Val Gly Trp
145                 150                 155                 160

Ile Arg Gln Pro Pro Gly Lys Ala Leu Glu Trp Leu Ala His Ile Trp
                165                 170                 175

Trp Glu Asp Asp Lys Tyr Tyr Asn Pro Ser Leu Lys Ser Arg Leu Thr
            180                 185                 190

Ile Thr Lys Asp Thr Ser Lys Asn Gln Val Val Leu Thr Met Thr Asn
        195                 200                 205

Met Asp Pro Val Asp Thr Ala Thr Tyr Tyr Cys Thr Arg Asn Trp Asp
        210                 215                 220

Tyr Tyr Thr Met Asp Tyr Trp Gly Gln Gly Thr Thr Val Thr Val Ser
225                 230                 235                 240

Ser
```